(12) United States Patent
Mangat

(10) Patent No.: US 7,498,169 B2
(45) Date of Patent: Mar. 3, 2009

(54) EXTENDING TISSUE PRESERVATION

(75) Inventor: Harpal S. Mangat, Tampa, FL (US)

(73) Assignee: University of South Florida, Tampa, FL (US)

( * ) Notice: Subject to any disclaimer, the term of this patent is extended or adjusted under 35 U.S.C. 154(b) by 190 days.

(21) Appl. No.: 10/752,472

(22) Filed: Jan. 6, 2004

(65) Prior Publication Data

US 2004/0142466 A1 Jul. 22, 2004

Related U.S. Application Data

(62) Division of application No. 10/013,898, filed on Nov. 29, 2001, now abandoned, which is a division of application No. 09/240,535, filed on Jan. 29, 1999, now abandoned.

(60) Provisional application No. 60/073,202, filed on Jan. 30, 1998.

(51) Int. Cl.
*C12N 5/06* (2006.01)
*C12N 5/08* (2006.01)

(52) U.S. Cl. ..................... 435/374; 435/366

(58) Field of Classification Search .............. 435/374, 435/366
See application file for complete search history.

(56) References Cited

U.S. PATENT DOCUMENTS

| | | | |
|---|---|---|---|
| 4,186,253 A | | 1/1980 | Yokoyama et al. |
| 4,452,818 A | * | 6/1984 | Haidt .......................... 514/747 |
| 4,490,351 A | * | 12/1984 | Clark, Jr. ..................... 424/9.4 |
| 4,666,828 A | | 5/1987 | Gusella |
| 4,683,202 A | | 7/1987 | Mullis |
| 4,801,531 A | | 1/1989 | Frossard |
| 5,004,681 A | | 4/1991 | Boyse et al. |
| 5,173,512 A | | 12/1992 | Meinert et al. |
| 5,192,659 A | | 3/1993 | Simons |
| 5,272,057 A | | 12/1993 | Smulson et al. |
| 5,702,881 A | | 12/1997 | Brasile et al. |
| 6,054,311 A | * | 4/2000 | Davey et al. ................. 435/260 |
| 6,490,880 B1 | | 12/2002 | Walsh |

OTHER PUBLICATIONS

Kuroda et al. "Mechanism of oxygenation of pancreas during preservation by two-layer (Euro-Collins solution/perfluorochemical) cold-storage method". Transplantation. Apr. 1990. vol. 49, No. 4, pp. 694-696.*
Green et al. "Perfluorocarbon liquid effects on corneal endothelial permeability". Lens and Eye Toxicity Research. 1992, 9 (1), pp. 1-8.*
Chapter Seven; The Cornea and Sclera; pp. 233-270, 1997. 8th. edition Bron AF. et al. Wolff's Anatomy of the Eye.
Balazs et al.; Vegetative Physiology and Biochemistry; The Eye; vol. 1a, 3rd Edition, pp. 1-259; 1984.
Riess, Jean G., Fluorocarbon-Based in vivo Oxygen Transport and Delivery Systems, Vox Sanguinis, 1991, 61, Abstract of p. 255-239.
Sambrook, J. et al., Molecular Cloning: A Laboratory Manual, Cold Spring Harbor Laboratory Press, 1989, New York., p. 1.
Ausubel, Frederick M. et al., Current Protocals in Molecular Biology, 1989, vol. 1, p. 1.
Casey, Thomas A., Corneal Grafting in Developing Countries, Principles & Practice of Corneal Grafting, 1984, p. 331-336.
Chang, Shu-Wen et al., The Epithelial Barrier Function in Clear Corneal Grafts, Ophthalmic Research, 1994, 26, p. 283-289.
Chen, Chung-Ho et al., The Efficacy of Non-Lactate-Generating Metabolites as Substrates for Maintaining Donor Tissues, Transplantation, 1994, V. 57 N. 12, p. 1778-1785.
Chen et al., Efficacy of Organ Preservation Media Enriched with Nonlactate-Generating Substrate for Maintaining Tissue Viability, Transplantation, 1997, 63:5, 656-663.
Clark, Leland C. et al., Survival of Mammals Breathing Organic Liquids Equilibrated with Oxygen at Atmospheric Pressure, F. Science, 1966; 152:1755.
Dellacherie, Edith et al., Synthetic Carriers of Oxygen, CRC Critical Reviews in Ther. Drug Carrier Systems, 1987, vol. 3 No. 1, p. 41-94.
Dikstein, S. et al., The Metabolic Basis to the Fluid Pump in the Cornea, J. of Physiology, 1972, vol. 221, 29-41.
Dunman, J.G. et al., Molecular Characterization and Sequencing of Antifreeze proteins from larvae of the beetle Dendroides Canadensis, J. of Comparative Physiolo.
Edelhauser, Henry E. et al., Cornea and Sclera, Biomedical Foundations of Ophthamology, 1982, vol. 2, Ch. 4 p. 1-26.
Faithfull, N.S. et al., Perfluorocarbon Compounds, Vox Sanguinis, 1998, vol. 74 (Suppl. 2), p. 243-248.

(Continued)

*Primary Examiner*—Vera Afremova
(74) *Attorney, Agent, or Firm*—Anton J. Hopen; Smith & Hopen, P.A.

(57) ABSTRACT

A method of sustaining cells is provided. The method can include providing a non-perfluorocarbon cell storage medium, providing a pre-oxygenated liquid perfluorocarbon in contact with the storage medium, and placing the cells in contact with the storage medium but not in contact with the perfluorocarbon. Additionally, the method can result in increased corneal cell viability compared to corneal cells placed in a non-perfluorocarbon cell storage medium without being in contact with a pre-oxygenated liquid perfluorocarbon.

17 Claims, 8 Drawing Sheets

OTHER PUBLICATIONS

Filatov, V.P., Transplantation of the Cornea from Preserved Cadavers Eyes, The Lancet, 1937, vol. 1, 1395-1397.

Gauthier, Sherry Y. et al., Disulfide bond mapping and structural characterization of spruce budworm antifreeze protein, Eur. J. Biochem., 1998, vol. 258, p. 445-453.

Gollan, Frank et al., Prevention of Bends by Breathing and Organic Liquid, Transactions of the Assoc. of Amer. Physicians, 1967, vol. 80, p. 102-110.

Gollan, Frank et al., Rapid Decompression of Mice Breathing Fluorocarbon Liquid at 500 PSI, Alabama Journal of Medical Sciences, 1967, vol. 4, No. 1, 336.

Holman et al., Use of Current Generation Perfluorocarbon Emulsions in Cardiac Surgery, Artif. Cells Blood Sub. and Immobil Biotechnology, 1994, vol. 22, No. 4, p. 979-990.

Report of the Organ Transplant Panel, JAMA, 1988, vol. 259, No. 5, p. 719-722.

Klen, R. et al., Use of the Anterior Chamber of the Eye for Selection and Preservation of Cornea, Amer. J. of Ophthalmology, 1965, vol. 60, 879-889.

Klyce, S.D. et al., The activation of chloride transport by epinephrine and Db cyclic-AMP in the cornea of the rabbit, Investigative Ophthalmology, 1973, 12(2), p. 127-139.

Klyce, S.D., Stromal Lactate Accumulation Can Account for Corneal Oedema Osmotically Following Epithelial Hypoxia in the Rabbit, J. of Physiology, vol. 321, p. 49-64.

Li, Ning et al., Enhancement of Insect Antifreeze Protein Activity by Solutes of Low Molecular Mass, J. of Experimental Biology, 1998, V. 201, 2243-2251.

Lane, Andrew H. et al., Conformational and dynamic properties of a 14 residue antifreeze glycopeptide from Antarctic cod, Protein Science, 1998, vol. 7, p. 1555-1563.

Maurice, D.M. Cellular Membrane Activity in the Corneal Endothelium of the Intact Eye, Experientia, 1968, V. 24, 1094-1095.

Maurice, D.M., Cornea and Sclera, The Eye, 1984, vol. 1b, p. 1-158.

Morton, Helen J., A Survey of Commercially Available Tissue Culture Media, In Vitro, 1970, vol. 6 No. 2, p. 89-108.

Nobuhara, Kerilyn K. et al., Long-Term Effect of Perfluorocabon Distension on the Lung, J. of Pediatric Surgery, 1998, vol. 33 No. 7, p. 1024-1029.

Parry, Ernest, Blood substitutes; historical perspective, Blood Substitutes Preparation, Physiology and Medical Applications, 1988, p. 17-50.

Patel, Shwetal et al., Modeling of Oxygen Transport in Blood-Perfluorocarbon Emulsion Mixtures Part II: Tissue Oxygenation, ASAIO Journal, 1998, vol. 44 No. 3, p. 157-165.

Peyman, Gholam A. et al., Perflourocarbon Liquids in Ophthalmology, Survey of Ophthalmology, 1995, vol. 39 No. 5, p. 375-395.

Porter, Thomas et al., The clinical implications of no reflow demonstrated with intravenous perfluorocarbon containing microbubbles, Amer. J. of Cardiology, 1998, 82, 1173-7.

Rao, Gullapalli et al., Recovery of Corneal Sensitivity in Grafts Following Penetrating Keratoplasty, Ophthalmology, 1985, 92(10), p. 1408-1411.

Redbrake, C. et al., Untersuchungen zum Energiestoffwechsel der humanen Hornhaut in verschiedenen Kultursystemen, Klinische Monatsblatter fur Augenheilkunde, 1997, 210(4).

Riess, J.G. et al., Perfluoro Compounds as Blood Substitutes, Angewandte Chemie, 1978, vol. 17, No. 9, p. 621-634.

Roscoe, W.R. et al., Corneal Oxygen Demands; A Comparison of the Open-and-Closed-Eye Environments, Amer. J. of Optometry & Physiological Optics, 1980, 57(2), 67-69.

Rutzky, Lynn P. et al., Supplement to a Survey of Commericially Available Tissue Culture Media, In Vitro, 1974, vol. 9 No. 6, p. 468-469.

Roycrofy, B.W., The Scope of Corneal Grafting, British J. of Ophthalmology, 1954, vol. 38, p. 1-9.

Slack, J.W. et al., Comparison of Corneal Preservation Media for Corneal Hydration and Stromal Proteoglycan Loss, Cornea, 1992, vol. 11 No. 3, p. 204-210.

Stocker, Frederick W. et al., Clinical Test for Evaluating Donor Corneas, Archives of Ophthal., 1970, vol. 84, p. 2-7.

Thoft, Richard A. et al., Corneal Epithelial Preservation, Archives of Ophthalmology, 1975, V. 93, p. 357-361.

Tugal Tutkun, I. et al., Corneal Sensitivity after Penetrating Keratoplasty, Euro. J. of Ophthalmology, 1993, V. 3 N. 2, p. 66-70.

Tyshenko, Michael G. et al., The antifreeze potential of the spruce budworm thermal hysteresis protein, Nature Biotechnology, 1997, v. 15, p. 887-890.

Van Horn, Diane L., Evaluation of Trypan Blue Staining of Human Corneal Endothelium, Corneal Preservation, 1973, p. 75-80.

Vannas, Antti et al., Epithelial metabolism of the corneal graft is abnormal, British J. Ophthalmology, 1987, v. 71, p. 593-597.

Ye, Qilu et al., Structure of type III antifreeze protein at 277K, Acta Crystallographica Section D Biological Crysrallographica, 1998, V. D54, p. 700-702.

* cited by examiner

EXTENDING TISSUE PRESERVATION

CROSS-REFERENCE TO RELATED APPLICATIONS

This application is a divisional of U.S. patent application Ser. No. 10/013,898, filed on Nov. 29, 2001, which is a divisional of U.S. patent application Ser. No. 09/240,535, filed on Jan. 29, 1999, which claims priority to U.S. Provisional Patent Application No. 60/073,202, filed Jan. 30, 1998. The entirety of each of the foregoing applications is herein incorporated by reference.

GOVERNMENT SUPPORT

Not Applicable.

BACKGROUND OF THE INVENTION

1. Technical Field

The present invention relates to the field of preservation of tissue for transplantation and more specifically to storage media that can extend tissue preservation.

2. Description of Related Art

Corneal transplantation is the most common form of organ transplantation practiced in the United States. Two procedures for transplantation are utilized. Penetrating keratoplasty is used in about 90% of the cases, with lamellar keratoplasty being utilized in the remaining situations. Demand for corneal transplantation exceeds the available supply of corneas. Advances in procurement and preservation must continue to meet this demand. JAMA 1988 Feb. 5; 259(5):719-22.

The need for corneal transplantation in the United States stems from conditions which effect the midstroma and endothelium. On a global basis the major blinding diseases stem from trachoma and vitamin A deficiency, both conditions of the superior stroma. Very often the areas in greatest need are places where steroids to modulate the immune response to the corneal transplant are unavailable and patient follow up is suboptimal for successful use for the lamellar grafting technique. Lamellar keratoplasty allows the corneal surgeon to transplant stroma and viable epithelial tissue while retaining the host endothelium and inferior stroma. The successful outcome of the surgery requires cornea with intact epithelium. Similarly, the Lasik Method requires cornea with intact, viable epithelium.

Perfluorocarbons:

Perfluorocarbons are inert materials that were initially manufactured as part of the Manhattan project (Reiss) at the end of World War II. They were initially used to encase uranium. Perfluorocarbons are polymers of carbon, fluorine and hydrogen. They uniquely have cavities in which gaseous oxygen and carbon dioxide fit (Reiss, 1991). In the emulsion form, they have a larger surface area for gaseous exchange (Reiss, 1978; Dellacherie 1987; Parry 1988). Reviewed by Faithfull and Weers 1998 Vox Sang 74: Suppl 2:243-8.

Gollan and Clark reported in 1966 and 1967 that mice could survive for prolonged periods immersed in oxygenated perfluorocarbons. However, toxicity later attributed to impurities, preventing development of medical applications. In the early 1980's high quality pure perfluorocarbons and emulsions were developed. Perfluorocarbons are currently used in cardiac applications (Porter et al. Am. J. Cardiol. 1998 Nov. 15:82(10) 1173-7. Liquid ventilation, i.e. postnatal long (Nobubara et al., 1998 J Pediatr Surg July 33(7) 1024-9, and artificial blood (Patel SASAIO) 1998 May-June: 44(3) 144-56; Cardiac Surgery Holman, et al., 1994 Artif Cells Blood Substit Immobil Biotechnol 22(4):979-90) and artificial blood uses of perfluorocarbons were pioneered by David Long in the late 1980's.

Perfluorocarbon liquids have been used in ophthalmology to facilitate surgery in a wide variety of conditions, including proliferative vitreoretinopathy, giant retinal tears, drainage of suprachoroidal hemorrhages, diabetic traction, retinal detachments with a rhegmatogenous component, dislocated crystalline or intraocular lenses, and retinal detachment associated with choroidal coloboma. The clarity of perfluorocarbon liquids, with a refractive index close to that of water, allows the use of a conventional contact lens for vitreous surgery while the low viscosity facilitates tissue manipulation, injection, and removal. All perfluorocarbon liquids when used as tamponading agents can compress and disorganize the retina. This "toxicity" is a physical effect rather than chemical toxicity and depends upon the amount of perfluorocarbon liquid injected. Perfluorocarbon liquids are not tolerated in the anterior chamber, causing corneal edema within two to three days at the site of contact. Peyman G A et al. Surv. Ophthalmol 1995 March-April:39(5):375-95

The concept of corneal transplantation is a hundred years old, the first successful transplant having been performed in 1897. The concept of increasing donor storage time by removing cadaver cornea and storing them in solutions was introduced by Filatov in 1937. Rycroft (Rycroft, 1954) and Beran (Beran, et al., 1958) extended corneal storage by placing cornea in liquid paraffin in the 1950's. Klen (Klen, et al., 1965) in the 1960's extended corneal transparency by insufflating air into the anterior chamber. In the early 1970's, cornea were stored in moist chambers for 24 hours.

The cornea is composed of five layers: epithelium, Bowmans layer, stroma, Descemets membrane and endothelium. It is a sandwich with the epithelium and endothelium being the bread slices and the stroma being the filling.

The stroma is made of parallel collagen fibrils arranged in lamellae (Edelhauser, et al., 1982; Tripathi et al., 1984; Maurice, 1984). These lamellar layers are arranged to create a pattern of destructive interference from one lamella to the other (Edelhauser, et al., 1982; Tripathi et al., 1984; Maurice, 1984), thereby maintaining corneal clarity.

Proteoglycans play an important role in the architectural integrity of these lamellae plates. In vivo the cornea is kept in a dehydrated form by the active aerobic endothelium pump. In hypoxic conditions the epithelium manufactures lactic acid. The acid diffuses into the stroma (Klyce, 1981), resulting in stromal swelling and loss of corneal clarity.

Cornea stored in media with reduced epithelial integrity lose more proteoglycans then those stored with intact epithelium (Slack, et al., 1992). The presence of intact corneal epithelium is required for maintaining the hydration and sodium levels within corneal strome during storage. Loss of epithelium results in increased sodium levels and hydration which may effect post keratoplasty deturgescense. (Jabulinski, 1998) In 1977 it was recognized that if enucleation could not be done within one hour of death, corneal epithelium viability could be ensured by placing ice over the eye (Thoft, et al., 1975).

Corneal oxygen uptake was less at the center of transplanted cornea compared to their control other eye (Vannas, et al., 1987). Epithelial permeability, e.g. damage, has been shown to be greater in these transplanted cornea when compared to the control other eye (Chang, et al., 1994). Others have demonstrated significant diminished corneal sensation at the center of the corneal graft (Tugaltutkun, et al., 1993; Rao, et al., 1985).

In 1974, McCarey & Kaufman realized the addition of glutathione to tissue culture fluid prolonged corneal storage to 72 hours (Roscoe, et al., 1980). Subsequent additions of chondroitin/dextran/and growth factor improved endothelial viability with little effect on corneal epithelium. Chen in 1994 showed the addition of beta-hydroxy butyrate diminished the lactic acid concentration of rabbit cornea by 85% without changing metabolic activity for at least 11 days (Chen, et al., 1994). Subsequent rabbit transplantation after 11 days storage in the Chen media showed corneas to be thin and clear with good endothelium (Chen, et al., 1997).

Beta hydroxybutyrate is an alternative energy source for the krebs cycle. The majority of the metabolism of the corneal metabolism is by the pentose shunt (Bron and Fielder) which in aerobic conditions produces NADPH, ribose and carbon dioxide. Chen has yet to address corneal epithelium issues especially those arising from hypoxia.

An appropriate medium that ensures survival of the corneal cholinergic system of the epithelia (Bron, et al., 1997 and Bron and Fielder) would reduce the likelihood of corneal anesthesia and preserve the viability of the corneal nerves. Preliminary data from perfluorocarbon addition prevents tissue hypoxia. It explains the observation of prolonged epithelial integrity. It may possibly prevent graft anesthesia by keeping the epithelial cholinergic system alive longer. This combination may enable corneal transplantation in other parts of the globe where steroids are not available with minimum medical follow up.

American Eye Banks are recognized as the most efficient in the world (Casey, 1984). Within the United States, approximately 39,000 people are awaiting for an organ transplant (70% for Kidneys). Social pressure has mandated reform for harvesting of tissue. In Pennsylvania, it resulted in act 102. This act made it mandatory that on every death or impending death, a member of the hospital staff had to call Delaware Valley transplant authority (DVTP). The DVTP would then procure organs for harvesting. This came into effect in March 1995. Within six months, Pennsylvania transformed itself from being an importer of cornea to an exporter. This is occurring throughout the nation.

In Europe eye banks developed later and differently. They tissue culture cornea at 33° C. for up to 28 days in MEM and then transport it in Eagles Medium for a further Review of financial data of University Louisville Eye Bank USA and Keratec Eye Bank UK). Redbrake et al. have shown anaerobic conditions to be the rate limiting step in prolonging corneal storage. It would therefore be useful to have an inexpensive storage media that can extend tissue preservation.

The demand for corneal tissue allows private Eye Banks (Keratec) to thrive. The ability to preserve corneal tissue for 35 days would allow the possibility of treating patients worldwide.

Currently no adequate media is available in the United States that can maintain endothelial and epithelial viability for 14 days. Should this become available, it would make the American Eye Banks highly competitive in the increasing global economy.

SUMMARY OF THE INVENTION

In one aspect of the invention, a method of sustaining cells can include providing a non-perfluorocarbon cell storage medium, providing a pre-oxygenated liquid perfluorocarbon in contact with the storage medium, and placing the cells in contact with the storage medium but not in contact with the perfluorocarbon. Additionally, the non-perfluorocarbon storage medium can form a layer on top of the perfluorocarbon and the cells can be completely immersed within the layer of the storage medium. The temperature of the storage medium can be maintained between −10° C. to 25° C.. Further, the temperature of the storage medium can be maintained at about 4° C..

In one embodiment, the perfluorocarbon can be at least five percent of the combined volume of the perfluorocarbon and the storage medium. The perfluorocarbon can be selected from the group consisting of a cyclical perfluorocarbon, a linear perfluorocarbon, and a neat perfluorocarbon. Additionally, the perfluorocarbon can be selected from the group consisting of perfluorodecalin, perfluorotripropylamine, perfluoro-N-methyl-decahydroisoquinoline, perfluoromethylcyclohexylpiperidine, perfluorodimethylcyclonanes and perfluoromethyladamantane. Further, the perfluorocarbon can be selected from the group consisting of perfluorooctylbromide, bis(perfluoro-butyl)ethane, perfluoro-octane, and perfluoro-octane. Additionally, the cells can be selected from the group consisting of corneal cells, sclera cells, retina cells, stem cells, and undifferentiated nervous cells.

In another aspect of the invention, a method for extending the viability of corneal cells that have been removed from a subject is provided. The method can include providing a non-perfluorocarbon cell storage medium, providing a pre-oxygenated liquid perfluorocarbon in contact with the storage medium, and placing the cells in contact with the storage medium but not in contact with the perfluorocarbon. The method can result in increased corneal cell viability compared to corneal cells placed in a non-perfluorocarbon cell storage medium without being in contact with a pre-oxygenated liquid perfluorocarbon. The method can also result in corneal cells having a lesser increase in corneal cell thickness compared to the increase in corneal cell thickness of corneal cells placed in a non-perfluorocarbon cell storage medium without being in contact with a pre-oxygenated liquid perfluorocarbon.

In another embodiment, the method can result in corneal cells of greater oxygen tension compared to the oxygen tension of corneal cells placed in a non-perfluorocarbon cell storage medium without being in contact with a pre-oxygenated liquid perfluorocarbon. Further, the method can result in corneal cells having a lesser mean lactic acid content compared to the mean lactic acid content of corneal cells placed in a non-perfluorocarbon cell storage medium without being in contact with a pre-oxygenated liquid perfluorocarbon.

In still another embodiment, the non-perfluorocarbon cell storage medium can include tryphan blue stain and the method can result in corneal cells of lesser tryphan blue staining compared to the tryphan blue staining of the corneal cells placed in a non-perfluorocarbon cell storage medium without being in contact with a pre-oxygenated liquid perfluorocarbon. The cells can be completely immersed within the layer of the storage medium. Also, the temperature of the storage medium can be maintained between −10° C. to 25° C.. Further, the temperature of the storage medium can be maintained at about 4° C..

In one arrangement, the perfluorocarbon can be at least five percent of the combined volume of the perfluorocarbon and the storage medium. Also, the perfluorocarbon can be selected from the group consisting of a cyclical perfluorocarbon, a linear perfluorocarbon, a neat perfluorocarbon, perfluorodecalin, perfluorotripropylamine, perfluoro-N-methyl-decahydroisoquinoline, perfluoromethylcyclohexylpiperidine, perfluorodimethylcyclonanes, perfluoromethyladamantane, perfluorooctylbromide, bis(perfluoro-butyl)ethane, perfluoro-octane, and perfluoro-octane.

DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
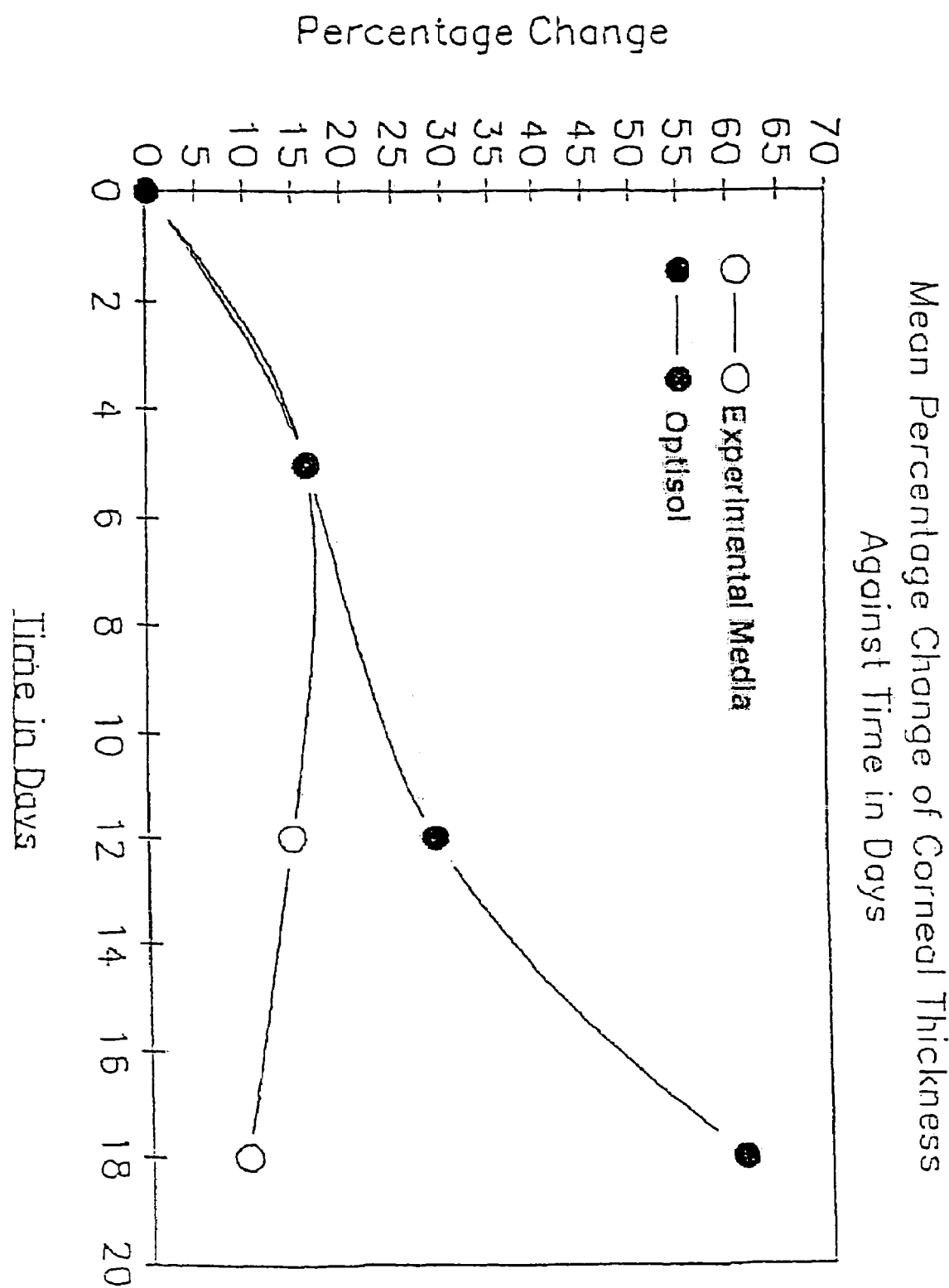
FIG. 1 is a graph showing the mean percentage change of corneal thickness against time in days for tissue stored in perfluorocarbon/Optisol or Optisol alone.
Figure 2:
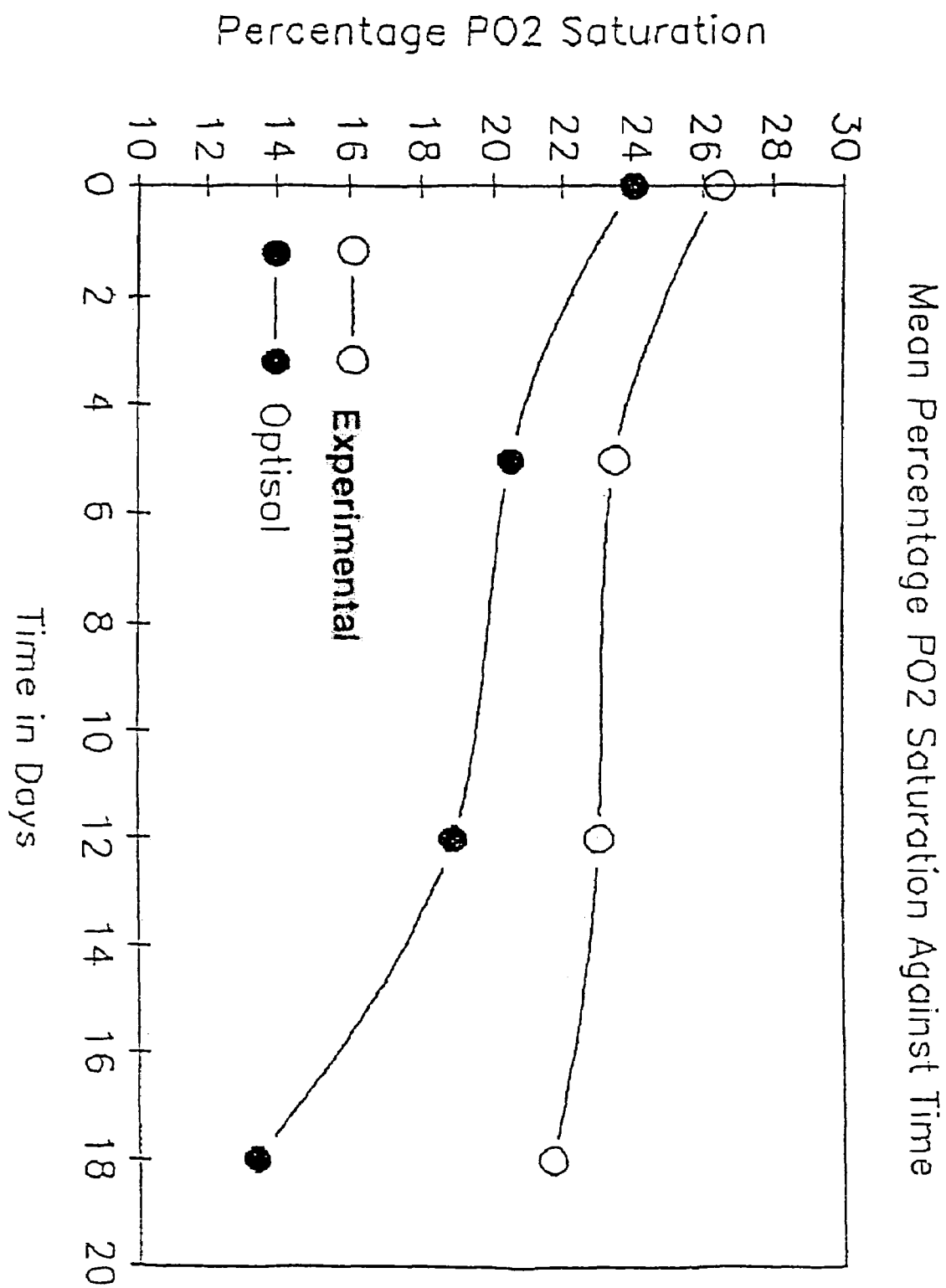
FIG. 2 is a graph showing the mean percentage/volume of dissolved $O_2$ in solution against time in days in corneas stored in perfluorocarbon/Optisol or Optisol.

Generally, the present invention provides a storage media for tissue preservation. In the preferred embodiment, the invention provides a storage media for corneas. The media maintains both corneal epithelial and endothelium in an optimum condition for at least 30 days at 4° Celsius.

More specifically, the present invention is a novel, non-perfusing technique for prolonging the preservation of tissue. The data has been gathered from corneal tissue, but the principles can be used to extend the viability of conjunctival, scleral, retinal, fetal, pancreatic, islets of Langerhans, liver and central nervous system tissue, occytes, embryos, cartilage, bone marrow and bone, hair grafts.

Retinal and fetal tissue are being increasingly used in transplantation, while central nervous system transplants are being used for treating Parkinson's disease, all of which can utilize the preservation principles of the present invention. The preservation principles of the present invention would also hold true for storage of blood, skin, muscle, tendons, nerve and cartilage, bone and bone marrow tissues intended for transplantation. Essentially the principle will be valid for any tissue desired to be preserved for transplantation, including newly developing synthetics lined with tissue, e.g., contact lenses lined with human corneal endothelium, heartvalves, artery and vein allografts.

The key additives are as pure as possible (i.e., 90% or greater) neat perfluorocarbon and/or perfluorocarbon emulsions. Perfluorocarbon is added to existing storage media to extend the media capacity for preservation of tissue. Existing storage media includes cell culture media, tissue culture media, cell storage media and tissue storage media, for example physiological buffered saline (PBS), Minimal Essential Media (MEM), Eagles Media M199, Optisol, Dexsol, McCarey-Kaufman medium, K-Sol, Corneal Storage Medium (CSM) or H-Sol. Additional media are described by Morton 1970 and Rutzky 1974. Perfluorocarbons carry gaseous oxygen ($O_2$) and carbon dioxide ($CO_2$) in their cavities (Reiss, 1991; Clark, et al. 1996; Golan, et al., 1967; Golan, et al., 1967; Reiss, et al., 1978; Dellacherie et al., 1987; Parry 1988). Their affinity for $CO_2$ is three times that of oxygen (Slack, et al., 1992). Added to storage media in the oxygenated form, they provide a reservoir of gaseous oxygen for aerobic metabolism and a carbon dioxide sink, mopping up $CO_2$ as it is produced, thus oxygenating the storage media. This prevents a build up of lactic acid and ensuing anaerobic metabolism. Hence perfluorocarbons extend the life support capacity of existing storage media. The small particle size of perfluorocarbon emulsions (e.g., 200 to 2,000 diameter) creates an increased surface area for gaseous exchange.

The perfluorocarbon media provides for longer tissue storage and enables transport of tissues from areas of surplus to areas of shortage.

Perfluorocarbons are inert, highly dense materials (1.8-2.0 g/ml) (Li et al., 1998), hence when added to aqueous based storage media, they sink to the bottom forming two layers with the perfluorocarbon at the bottom. Their oxygen solubility increases with decreasing temperature (Reiss, 1991).

In another embodiment, antifreeze proteins (Gauthier, et al., 1998; Ye, et al., 1998; Duman, et al., 1988; Tyshenko, et al., 1997) are added to the perfluorocarbon media to allow tissues immersed in such media to be placed in the freezer component of conventional refrigerators. The thermal hysteresis produced by antifreeze proteins and compounded by certain solutes (Li, et al., 1998) prevents ice crystal formation. The combination of increased oxygen reservoir in the perfluorocarbons at diminished temperature (Reiss, 1991) and the use of antifreeze proteins (Gauthier, et al., 1998; Ye, et al., 1998; Duman, et al., 1988; Tyshenko, et al., 1997) with additive solutes (Li, et al., 1998) enable tissues to be preserved for longer than currently possible.

These anti-freeze proteins can be further enhanced by the addition of low molecular weight solutes (Li, et al., 1998). Citrate can increase thermal hysteresis nearly six-fold (Li, et al., 1998) while addition of succinate, malate, aspartate, glutamate and ammonium sulfate increases thermal hysteresis by four-fold (Li, et al., 1998). Glycerol, sorbitol, alanine and ammonium bicarbonate increase activity by three-fold (Li, et al., 1998).

Tissue preservation requires as pure as possible perfluorocarbons (90% and above). They may be neat or emulsified into particles. The perfluorocarbon may be: cyclical e.g. perfluorodecalin, perfluorotripropylamine, perfluoro-N-methyl-decahydroisoquinoline, perfluoromethylcyclohexylpiperidine, perfluorodimethylcyclonanes or perfluoromethyladamantane; or linear polymers e.g. perfluorooctyl bromide, or bis(perfluoro-butyl) ethene perfluoro-octane or perfluoro-octane. The perfluorocarbon may be incorporated into the storage media individually or in any mixture so long as they are pure, neat or emulsified into small particles.

The preferred perfluorocarbon is a mixture of perfluorodecalin and perfluorotrinpropylamide. Emulsions have been made in a mixture of phosphatidylcholine, phosphatidylethanolamine and poloxamer 188. The emulsion particle size is approximately 2000 angstroms. The emulsion is buffered by physiological pH e.g., with bicarbonate buffer. In the preferred embodiment, this buffered perfluorocarbon emulsion is oxygenated by bubbling 100% oxygen or an oxygen, $CO_2$ mixture (i.e. 95% oxygen, 5% $CO_2$) through the emulsion until 100% saturation is achieved as measured with an oximeter.

In the preferred embodiment the perfluorocarbon is added to a storage media in a volume ratio of anywhere between 1-95%, generally 5 to 30%, preferably 10%. The exact amount depends upon the perfluorocarbon, the desired oxygen reserve, the carbon dioxide sink effect required, tissue being stored, and the preservation time required. This can be determined by one skilled in the art of tissue preservation.

The perfluorocarbon is added to storage media and the perfluorocarbon settles to the bottom of the storage container with a layer of media on top. The preparation is stored at temperatures ranging from −10° C. to 25° C., generally from 0° C. to 4° C., preferably 4° C.. The exact temperature is determined by the nature of the tissue, the freezing point of the mixture and the desired preservation time, and whether antifreeze protein and/or solutes are used in conjunction with perfluorocarbons to prevent ice crystal formation. The precise temperature can be determined by one skilled in the art of tissue preservation.

The above discussion provides a factual basis for the use of extending tissue preservation. The methods used with and the utility of the present invention can be shown by the following non-limiting examples and accompanying figures.

EXAMPLES

General Methods:

General methods in molecular biology: Standard molecular biology techniques known in the art and not specifically described were generally followed as in Sambrook et al., *Molecular Cloning: A Laboratory Manual,* Cold Spring Harbor Laboratory Press, New York (1989), and in Ausubel et al., *Current Protocols in Molecular Biology,* John Wiley and Sons, Baltimore, Md. (1989) and methodology as set forth in U.S. Pat. Nos. 4,666,828; 4,683,202; 4,801,531; 5,192,659 and 5,272,057 and incorporated herein by reference.

Example 1

Seven white New Zealand rabbits weighing two-three kg were killed with sodium pentobarbital overdose. Their eyes were flooded with neosporin. Corneas were excised from both eyes within ten minutes of termination. The right cornea were placed in a mixture of oxygenated perfluorocarbon emulsion and Optisol. The left eyes were placed in pure Optisol. In both cases the corneas were immersed in the Optisol layer. All corneas were stored at 4° C. for 20 days. The corneal thickness was measured using the Dickstein-Maurice technique with a pre-calibrated specular microscope. Central cornea measurements were on days 0, 6, 12 and 18 (average of three measurements). The oxygen tension was measured using a Yellow Spring oxygen electrode. Care was taken to ensure the reading was done at the level of the cornea. Results are the average of readings taken at the 4, 8 and 12 o'clock position on days 0, 6, 12 and 18. On day 21, lactic acid was measured as follows. The corneas were weighed minced in 4 ml of trichloroacetic acid at 0° C. and centrifuged at 1700 g for 15 minutes. The supernatant was collected and the lactic acid measured using a Sigma kit. The lactic acid concentration data was analyzed using a paired t-test. Repeated measure analysis of the corneal thickness and oxygen tension data was performed.

Paired human corneas were donated by the Kentucky Lions Eye Bank. Right human corneas were placed in a 10% by volume perfluorocarbon emulsion/Optisol mixture, left corneas were placed in Optisol. Care was taken to ensure the corneas remained in the Optisol layer. All corneas were stored at 4° C. On days 21, 25, 28 and 34 the corneal endothelium was stained with 0.25% tryphan blue in normal saline for 1.5 minutes and then viewed through a phase contrast microscope to assess viability.

Results

The standard test for evaluating corneal function is corneal thickness (Maurice, 1968; Dikstein, et al., 1972; Stocker, et al., 1970), and tryphan blue staining of the endothelium (Stocker et al., 1970; Van Horn, 1972).

There was a significant difference in the increase in corneal thickness between tissues stored in perfluorocarbon/Optisol or Optisol P=0.003. On day 18, the increase in corneal thickness in the perfluorocarbon/Optisol group was 10% v 61% in the Optisol group.

There is also a significant difference in dissolved oxygen content P=0.0001 between the perfluorocarbon/Optisol and Optisol groups. The mean oxygen tension on day 18 in the perfluorocarbon group was 20.9% v 13.85% in the Optisol group.

There was a significant difference in the lactic acid content of the two groups P=0.015. The mean lactic acid in the perfluorocarbon group was 26.18 mg/dl v 51.38 mg/dl in the Optisol group.

Figure 3:
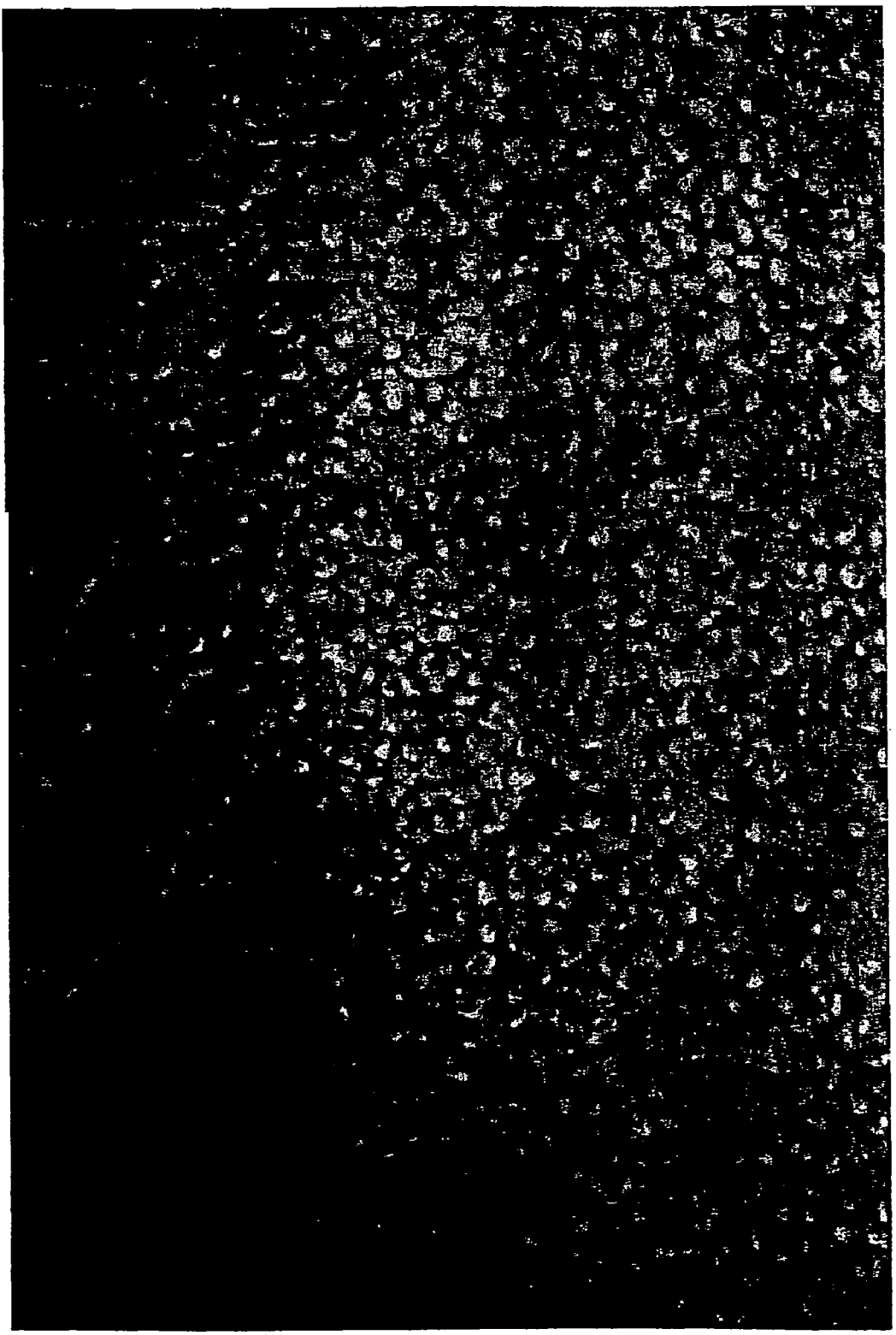
FIG. 3 is a photograph showing tryphan blue stained human corneal endothelial cells from tissue stored in perfluorocarbon/Optisol media for 34 days.
Figure 4:
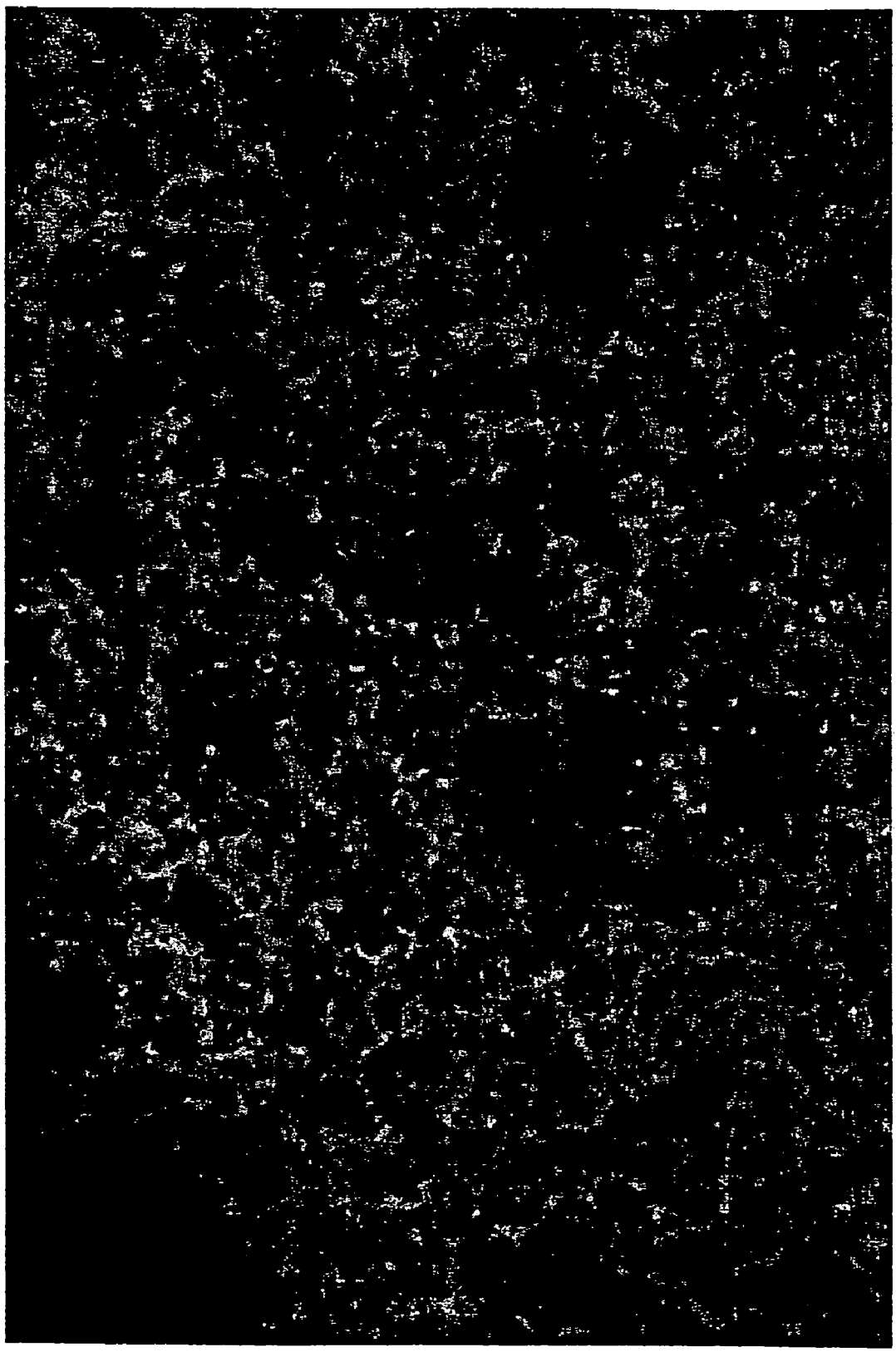
FIG. 4 is a photograph showing tryphan blue stained human corneal endothelial cells from tissue stored in Optisol for 34 days.
Figure 5:
FIG. 5 is a photograph showing human corneal endothelial cells, tryphan blue stained, from tissue stored in perfluorocarbon/Optisol media for 28 days.
Figure 6:
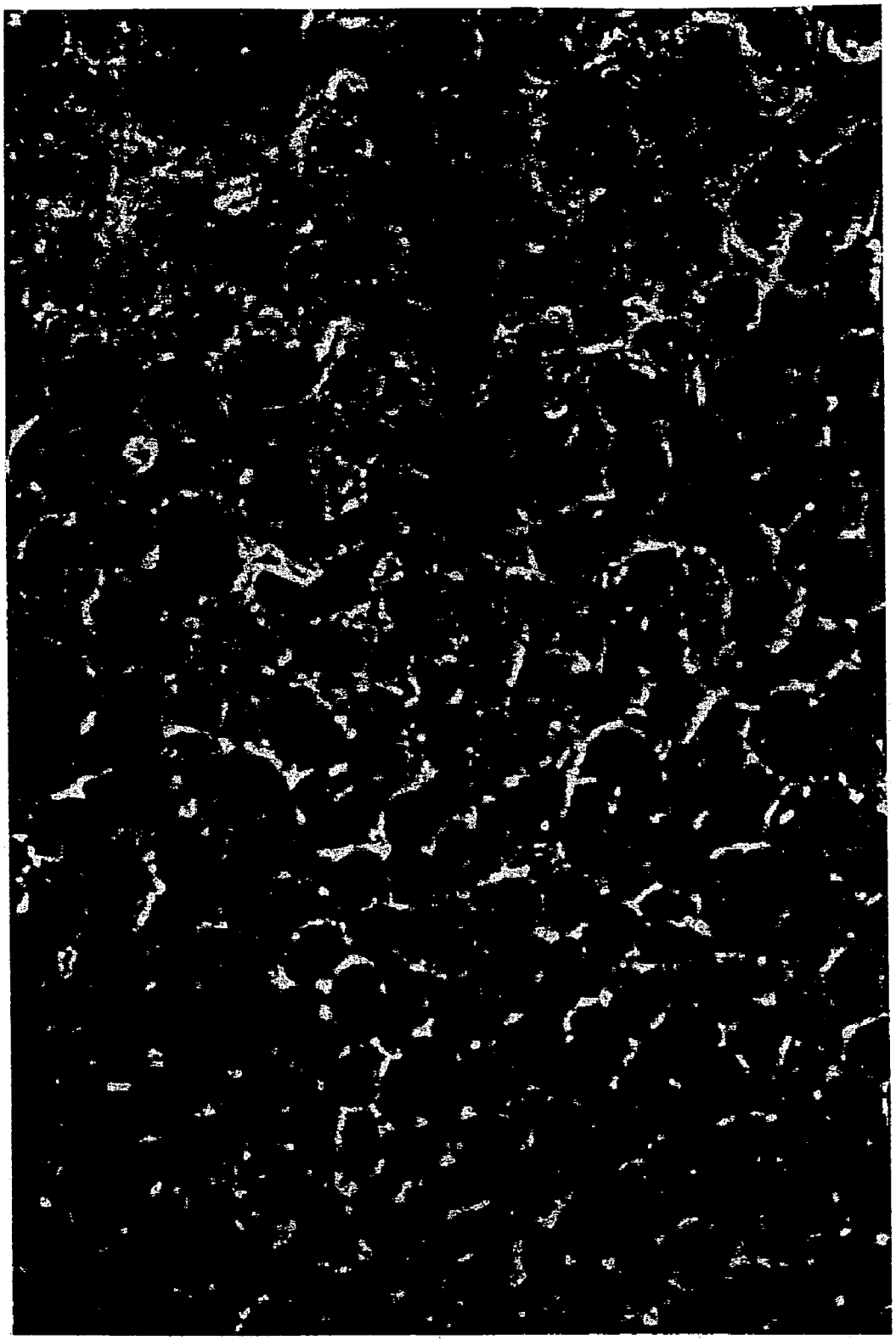
FIG. 6 is a photograph showing human corneal endothelial cell, tryphan blue stained, from tissue stored in Optisol for 28 days.
Figure 7:
FIG. 7 is a photograph showing human corneal endothelial cells, tryphan blue stained, from tissue stored in perfluorocarbon/Optisol media for 21 days.
Figure 8:
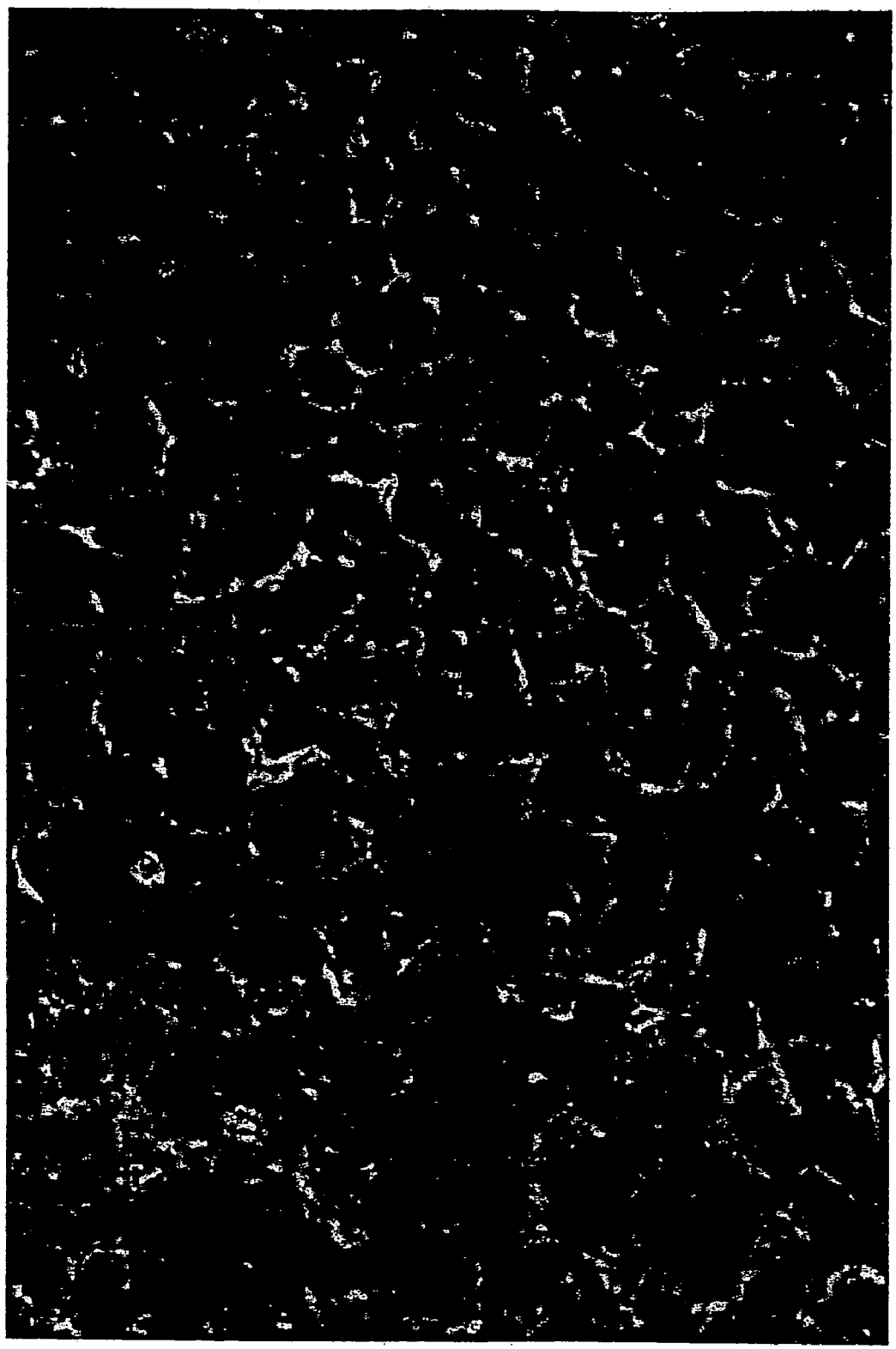
FIG. 8 is a photograph showing human corneal endothelial cells, tryphan blue stained, from tissue stored in Optisol for 21 days.

The human corneas stored in Optisol group showed uptake of tryphan blue stain in the endothelium on day 21 and by day 34 cells remaining were heavily stained. There was no tryphan blue staining in the human endothelial cells stored in the perfluorocarbon/Optisol media. (FIGS. 3-8).

Microscopically, it was noted that the corneal epithelium was maintained for a longer period of time in the perfluorocarbon/Optisol group than in the Optisol group.

CONCLUSIONS

Media containing oxygenated perfluorocarbon emulsions provided enhanced maintenance of corneal ultrastructure as demonstrated by tryphan blue staining and corneal thickness measurements. Desired oxygen content of the tissue was increased and lactic acid concentration was decreased suggesting aerobic metabolism in corneal tissue was maintained. Maintenance of corneal epithelium and endothelium was improved.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

1. Edelhauser H F et al. Cornea and Sclera Biomedical Foundations of Ophthalmology Vol. 2 Ch. 4. Editors Duane EA and Jaeger. 1982.

2. Tripathi R, Tripathi B J. Anatomy of the Orbit and Adnexa of the human eye. Editor Davson H. Vol. 19. Academic Press. 1984.

3. Maurice D M. The Cornea and Sclera in the Eye. Editor Davson H. Vol. 1b. Academic Press. 1984.

4. Klyce S D. Stromal Lactate accumulation can account for corneal edema osmotically following epithelial hypoxia in rabbits. J. of Physiology 321:49-64. 1981.

5. Slack J W, Kangas T F, Edelhauser H F et al. Comparison of Corneal Preservation media for corneal hydration and stromal proteoglycan loss. Cornea 11(3):204-210. 1992.

6. Thoft R A, Friend J, Freedman H, Dohlman C H. Corneal epithelial preservation. Arch. Ophthalmol. 93(5):357-361. 1975.

7. Vannas A, Holden B A, Sweeney D F: Epithelial metabolism of the corneal graft is abnormal. Br. J. Ophthalmol. 71(8):593-597. 1987.

8. Chang S W, Hu F R. The epithelial barrier function in clear corneal grafts. Ophthalmic Res. 26(5):283-289. 1994.

9. Tugaltutkun I, Akarcay K, Kozerbilgin L, et al. Corneal sensitivity after penetrating keratoplasty. Eur. J. Ophthalmol. 3(2):66-70. 1993.

10. Rao G N, John T, Ishida N, Aquavella J V. Recovery of corneal sensitivity in grafts following penetrating keratoplasty. Ophthalmology 92(10): 1408-1411. 1985.

11. Roscoe W R, Hill R M. Corneal oxygen demands a comparison of the open and closed environments. Am J Optom Physiol Opt 57(2):67-69. 1980.

12. Chen C H, Chen S C. The efficacy of non-lactate generating metabolites as substrates for maintaining donor tissues. Transplantation 57(12):1776-1785. 1994.

13. Chen C H, Rama P, Chen S C, Sansoy F N. Efficacy of organ preservation media enriched with nonlactate generating substrate for maintaining tissue viability: a transplantation study. Transplantation 63(5):656-663. 1997.

14. Casey T. Principles and Practice of corneal grafting 331-336 first edition pub W B Saunders 1984.

15. Insight Magazine EBAA 1994.

16. Review of financial data University Louisville Eye Bank USA and Keratec Eye Bank UK.

17. Bron A J, Tripathi R, Tripathi B J. Cornea and Sclera. Wolff's Anatomy of the Eye eighth edition 233-279. 1997.

18. Bron A J, Fielder A. Basic Science Course for FRCOphth part I. Oxford University, England.

19. Klyce S D, Neufeld A H, Zadunaisky J A. The activation of chloride transport by epinephrine and Db cyclic-AMP in the cornea of the rabbit. IOVS 20:194.

20. Filatov V P. Transplantation of cornea from preserved cadaver's eyes. 232:1395. 1937.

21. Rycroft B W. The Scope of corneal grafting Br. J. Ophthalm 38:109. 1954.

22. Beran J, Kien R, Klenova V. Corneal preservation in paraffin oil. Prace Vla 7:78. 1958.

23. Klen R, Klenova V, Pazderka J. Use of the anterior chamber of the eye for selection and preservation of the cornea. Am. J. Ophthalm. 60:88. 1965.

24. Reiss J G. Fluorocarbon based in vivo oxygen transport and delivery systems. Vox Sanguinis 61:225-239. 1991.

25. Clark L C, Gollan F. Science 152:755. 1966.

26. Gollan F, Clark L C. Trans. Assoc. Amer. Phys. 31:102. 1967.

27. Gollan F, Clark L C. Ala. J. Med. Sc. 4:336. 1967.

28. Reiss J G, Leblanc M. Perfluorocompounds in blood substitutes. Agw. Chem. (Int. edition in English) 17:621-634. 1978.

29. Dellacherie E, Labrude P, Vigneron C, Reiss J G. Synthetic carriers of oxygen. Crc Crit. Rev. Ther. Drug Carrier Syst. 3:41-94. 1987.

30. Parry E. Blood substitutes historical perspective: Blood substitutes, Preparation physiology and medical applications 17-50 vol 9 pub Horwood, Chichester. 1988.

31. Reiss J G. Re-assessment of the criteria for selection of perfluorochemicals for second generation blood substitutes: analysis of structure/property relationships. Artificial Organs 8(11):44-56.

32. Maurice D M. Cellular membrane activity in the corneal endothelium of the intact eye. Experienta 24:1094. 1968.

33. Dikstein S, Maurice D M. The Metabolic basis to the fluid pump in the cornea. J of Physiol 221:29. 1972.

34. Stocker F W, King E H, Lucas D O et al. Clinical Test for evaluating donor corneas Arch. Opthalm. 84:2. 1970.

35. Van Horn, D L. Evaluation of tryphan blue staining of human corneal endothelium. Corneal Preservation 75-80. Editors Capella J A, Edelhauser H F, Van Horn Publishers Charles C Thomas Springfield Ill. 1972.

36. Gauthier S Y, Kay C M et al. Disulfide bond mapping and structural characterization of spruce budworm antifreeze protein. Eur J. Biochem. 1998, Dec 1. 258(2):445-53.

37. Ye, Q, Leinala E, Jia Z. Structure of type III antifreeze protein at 277K. Acta Crystallogr D Biol Crystallogr 1998 Jul. 1:54 (Pt 4): 700-2.

38. Duman J G, Li N, et al. Molecular characterization and sequencing of antifreeze proteins from larvae of the beetle Dendroides canadensis. J Comp Physiol [B] 1988 April 168 (3):225-32.

39. Tyshenko M G, Doucet D, Davies P L, Walker V K. The antifreeze potential of the spruce budworm thermal hysteresis protein. Nat Biotechnol 1997 Sep. 15(9):887-90.

40. Li N, Andorfer C A, Duman J G. Enhancement of insect antifreeze protein activity by solutes of low molecular mass. J Exp Biol 1998 August 201 (Pt 15):2243-51. residue antifreeze glycopeptide from Antarctic cod. Protein Sci 1998 Jul. 7(7):1555-63.

41. Sambrook et al., *Molecular Cloning: A Laboratory Manual,* Cold Spring Harbor Laboratory Press, New York (1989).

42. Ausubel et al., *Current Protocols in Molecular Biology,* John Wiley and Sons, Baltimore, Md. (1989).

43. JAMA 1988 Feb. 5;259(5):719-22.

44. Reidbrach, C. S. Energy metabolism of the human cornea in various culture systems. Klinmonatspl augenheilk 1997 April 210(4):21328.

45. Rutzky, L. P., et al. In vitro 1974 May-June: 9(6):408-9.

46. Morton, H. J., In vitro 1970 September-October: 6(2) 89-108.

47. Faithfull & Weers 1998 Vox Sang 74: Suppl 2:243-8.

48. Porter et al. Am. J. Cardiol 1988 Nov. 15:82(10)1173-7.

49. Nobubara et al, 1998 J Pedistr Surg July 33(7) 1024-9

50. Patel SAS AIO 1988 May-June 44(3)144-56.

51. Holman et al. 1994 Artif Cells Blood Substit Immobil Biotechnol 22(4):979-90.

52. Peyman G A et al. Surv Ophthalmol 1995 March-April 39(5):375-95.

What is claimed is:

1. A method of sustaining corneal cells, comprising the steps of:
   providing a non-perfluorocarbon cell storage medium;
   providing a pre-oxygenated liquid perfluorocarbon underlayer in contact with the storage medium;
   submersing the corneal cells in the storage medium while not contacting the perfluorocarbon; and
   storing the cells at a temperature between $-10°$ C. to $25°$ C.

2. The method according to claim 1, wherein the non-perfluorocarbon storage medium forms a layer on top of the perfluorocarbon.

3. The method according to claim 1, wherein the temperature of the storage medium is maintained at about 4° C.

4. The method according to claim 1, wherein the perfluorocarbon is selected from the group consisting of perfluorooctylbromide, bis(perfluoro-butyl)ethane, and perfluorooctane.

5. A method for extending the viability of corneal cells that have been removed from a subject, comprising the steps of:
   providing a non-perfluorocarbon cell storage medium;
   providing a pre-oxygenated liquid perfluorocarbon in contact with the storage medium;
   submersing the corneal cells in the storage medium while preventing contact with the perfluorocarbon; and
   storing the cells at a temperature between −10° C. to 25° C.

6. The method according to claim 5, wherein the temperature of the storage medium is maintained at about 4° C.

7. The method according to claim 1, wherein the perfluorocarbon is about 5% to about 30% of the combined volume of the perfluorocarbon and the storage media.

8. The method according to claim 1, wherein the perfluorocarbon is selected from the group consisting of perfluorodecalin, perfluorotripropylamine, perfluoro N-methyldecahydroisoquinoline, perfluoromethylcyclohexylpiperidine and perfluorodimethylcyclonane.

9. The method according to claim 5, wherein the perfluorocarbon is selected from the group consisting of a perfluorodecalin, perfluorotripropylamine, perfluoro N-methyldecahydroisoquinoline, perfluoromethylcyclohexylpiperidine and perfluorodimethylcyclonane.

10. The method according to claim 5, wherein the non-perfluorocarbon cell storage medium is corneal storage medium.

11. The method according to claim 10, wherein the corneal storage medium is selected from the group consisting of Optisol, K-Sol, Dexsol, H-Sol, McCarey-Kaufman medium, Corneal Storage Medium, Eagles Media M199, Minimal Essential Media and Phosphate Buffered Saline.

12. The method according to claim 5, wherein the non-perfluorocarbon cell storage medium is Optisol.

13. The method according to claim 1 wherein the cells are sustained in the absence of substantially continuous oxygen bubbling.

14. The method according to claim 5 wherein the cells are maintained in the absence of substantially continuous oxygen bubbling.

15. The method according to claim 1, wherein the cells are completely immersed within the layer of the storage medium.

16. The method according to claim 1, wherein the cells are maintained at about 0° C. to about 4° C.

17. The method according to claim 5, wherein the cells are maintained at about 0° C. to about 4° C.

* * * * *